United States Patent
Conley et al.

(10) Patent No.: US 6,449,504 B1
(45) Date of Patent: Sep. 10, 2002

(54) ARRHYTHMIA DISPLAY

(75) Inventors: Vickie L. Conley, Woodbury; Allan T. Koshiol, Lino Lakes, both of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/382,292

(22) Filed: Aug. 24, 1999

Related U.S. Application Data

(63) Continuation-in-part of application No. 09/378,030, filed on Aug. 20, 1999.

(51) Int. Cl.$^7$ .............................................. A61B 5/044
(52) U.S. Cl. ...................................................... 600/523
(58) Field of Search ................................. 600/523, 509, 600/515; 607/5, 14

(56) References Cited

U.S. PATENT DOCUMENTS

| | | | |
|---|---|---|---|
| 4,006,737 A | 2/1977 | Cherry .................. 128/2.06 G |
| 4,090,505 A | 5/1978 | Mortara ................. 128/2.06 G |
| 4,166,470 A | 9/1979 | Neumann ............. 128/419 PG |
| 4,172,459 A | 10/1979 | Hepp .......................... 128/697 |
| 4,187,854 A | 2/1980 | Hepp et al. ........... 128/419 PG |
| 4,316,249 A | 2/1982 | Gallant et al. ............... 364/417 |
| 4,336,810 A | 6/1982 | Anderson et al. ........... 128/702 |
| 4,509,530 A | 4/1985 | Curtis et al. ................. 128/710 |
| 4,549,552 A | 10/1985 | Groch et al. ................. 128/700 |
| 4,680,708 A | 7/1987 | Ambos et al. ............... 364/417 |
| 4,947,857 A | 8/1990 | Albert et al. ................ 128/696 |
| 4,974,598 A | 12/1990 | John .......................... 128/696 |
| 5,012,814 A | 5/1991 | Mills et al. .................. 128/691 |
| 5,027,824 A | 7/1991 | Dougherty et al. .......... 128/702 |
| 5,046,504 A | 9/1991 | Albert et al. ................ 128/696 |
| 5,047,930 A | 9/1991 | Martens et al. ........ 364/413.04 |
| 5,050,612 A | 9/1991 | Matsumura .................. 128/670 |
| 5,052,395 A | 10/1991 | Burton et al. ........... 128/661.09 |
| 5,113,869 A | 5/1992 | Nappholz et al. ............ 128/696 |
| 5,299,118 A | 3/1994 | Martens et al. ........ 364/413.05 |
| 5,309,919 A | 5/1994 | Snell et al. .................. 128/697 |
| 5,311,873 A | 5/1994 | Savard et al. ................ 128/696 |
| 5,315,512 A | 5/1994 | Roth ...................... 364/413.25 |
| 5,341,811 A | 8/1994 | Cano ........................... 128/696 |
| 5,342,402 A | 8/1994 | Olson et al. ................... 607/5 |
| 5,487,754 A | 1/1996 | Snell et al. .................... 607/27 |
| 5,487,755 A | 1/1996 | Snell et al. .................... 607/27 |
| 5,513,645 A | 5/1996 | Jacobson et al. ............ 128/710 |
| 5,535,753 A | 7/1996 | Petrucelli et al. ............ 128/672 |
| 5,555,888 A | 9/1996 | Brewer et al. ............... 128/702 |
| 5,584,298 A | 12/1996 | Kabal .......................... 128/672 |
| 5,613,495 A | 3/1997 | Mills et al. .................. 128/696 |
| 5,626,620 A | 5/1997 | Kieval et al. ................... 607/9 |
| 5,626,623 A | 5/1997 | Kieval et al. .................. 607/23 |
| 5,628,321 A | 5/1997 | Scheib et al. ........... 128/661.08 |
| 5,643,255 A | 7/1997 | Organ ........................... 606/41 |
| 5,647,369 A | 7/1997 | Petrucelli et al. ............ 128/672 |
| 5,683,431 A | 11/1997 | Wang ............................ 607/28 |
| 5,687,737 A | 11/1997 | Branham et al. ............ 128/710 |
| 5,697,959 A | 12/1997 | Poore ........................... 607/32 |
| 5,713,366 A | * 2/1998 | Armstrong et al. |
| 5,716,383 A | 2/1998 | Kieval et al. ................... 607/9 |
| 5,716,384 A | 2/1998 | Snell ............................ 607/30 |
| 5,722,999 A | 3/1998 | Snell ............................ 607/32 |
| 5,724,985 A | 3/1998 | Snell et al. .................. 128/697 |

(List continued on next page.)

FOREIGN PATENT DOCUMENTS

EP          0565084          10/1993         ......... A61B/5/0452

*Primary Examiner*—Jeffrey R. Jastrzab
(74) *Attorney, Agent, or Firm*—Schwegman, Lundberg, Woessner & Kluth, P.A.

(57) ABSTRACT

Systems, devices, structures, and methods are provided to present a visual display based on data from an implantable medical device. The display includes a chart showing the frequency of a detected type of arrhythmia over a predetermined period of time.

45 Claims, 6 Drawing Sheets

U.S. PATENT DOCUMENTS

| | | | |
|---|---|---|---|
| 5,743,268 A | 4/1998 | Kabal | 128/691 |
| 5,749,906 A | 5/1998 | Kieval et al. | 607/9 |
| 5,749,907 A | 5/1998 | Mann | 607/27 |
| 5,772,604 A | 6/1998 | Langberg et al. | 600/518 |
| 5,788,640 A | 8/1998 | Peters | 600/483 |
| 5,792,204 A | 8/1998 | Snell | 607/32 |
| 5,817,137 A | 10/1998 | Kaemmerer | 607/59 |
| 5,833,623 A | 11/1998 | Mann et al. | 600/523 |
| 5,891,179 A | 4/1999 | Er et al. | 607/27 |
| 5,924,989 A | 7/1999 | Polz | 600/443 |
| 5,951,484 A | 9/1999 | Hoium et al. | 600/515 |
| 5,954,664 A | 9/1999 | Seegobin | 600/515 |
| 5,961,467 A | 10/1999 | Shimazu et al. | 600/485 |
| 5,974,341 A | 10/1999 | Er et al. | 607/31 |
| 6,004,276 A | 12/1999 | Wright et al. | 600/508 |
| 6,016,442 A | 1/2000 | Hsu et al. | 600/518 |
| 6,017,307 A | 1/2000 | Raines | 600/300 |

\* cited by examiner

ARRHYTHMIA DISPLAY

CROSS REFERENCE TO RELATED APPLICATIONS

This application is a continuation-in-part of U.S. patent application Ser. No. 09/378,030, filed on Aug. 20, 1999, the specification of which is incorporated herein by reference.

TECHNICAL FIELD

The present invention relates generally to implantable medical devices. More particularly, it pertains to displaying arrhythmia episodes based on data taken from implantable medical devices.

BACKGROUND INFORMATION

A normal human heart beats between 60 to 100 times per minute. However, when a person gets excited or frightened or has an illness such as congenital heart disease, the heart may beat faster than 100 times per minute. A disruption in the normal heart rate or rhythm is known as arrhythmia.

Arrhythmias are caused by abnormal functioning of the electrical conduction of the heart. Normally, the chambers of the heart (atria and ventricles) work in a coordinated manner. The electrical conduction begins with an electrical impulse originating in the sinoatrial node. This impulse is then moved through the atria, stimulates them to contract, and then is moved to its final destination at the ventricles, where it stimulates them to contract also. Any problems along this conduction path may cause arrhythmias.

Certain types of arrhythmia are lethal and may cause severe damage to various organs in the body by initially decreasing the pumping of the heart. When the pumping of the heart is decreased by more than a few seconds, blood circulation is essentially stopped, and organ damage (such as brain damage) may occur within a few minutes.

Arrhythmias have been treated by the use of a pacemaker that applies shock therapy. A pacemaker is a medical device that delivers controlled electrical pulses to an electrode that is implanted adjacent to or in the heart. These controlled electrical pulses stimulate the heart so that it will contract and beat at a desired rate. The delivery of these controlled electrical pulses is often tailored to the individual patient.

A physician at times needs to reassess the therapy applied by the pacemaker. One technique is for the physician to obtain a printed listing of the therapy data from the pacemaker and reformulate the therapy. However, what has been frustrating for the physician is that the use of the listing of data to reformulate the therapy has been laborious, time-intensive, and error-prone.

Thus, what is needed are systems, devices, structures, and methods to ease the use of the therapy data by a physician.

SUMMARY

The above-mentioned problems with the use of data from an implantable medical device as well as other problems are addressed by the present invention and will be understood by reading and studying the following specification. Systems, devices, structures, and methods are described which ease the use of therapy data by a physician.

In particular, an illustrative embodiment includes an exemplary display. This display comprises a first graph to show a frequency of at least one type of ventricular arrhythmia over a predetermined amount of time. The display also comprises a second graph to show a frequency of at least one type of atrial arrhythmia over the predetermined amount of time.

Another illustrative embodiment includes an exemplary method of performing a medical diagnostic. The method comprises receiving data stored in an implantable medical device, viewing a display that includes at least one graph showing the frequency of at least one type of arrhythmia over a predetermined period of time. The graph is formed from the data received from the implantable medical device. The method further comprises deriving a diagnostic based at least on the graph.

A further illustrative embodiment includes an exemplary method of therapy. The method comprises viewing a display that includes at least one graph showing the frequency of at least one type of arrhythmia over a predetermined period of time. The method further comprises deriving a set of programming variable values based at least on the graph to program an implantable medical device. The method further comprises transmitting the set of programming variable values to the implantable medical device so as to apply a therapy when a patient experiences a predetermined type of arrhythmia.

A further illustrative embodiment includes an exemplary system. The system comprises an implantable medical device. The implantable medical device includes a controller to control the implantable medical device, memory coupled to the controller to store at least one occurrence of at least one type of arrhythmia over a predetermined period of time, and a medical device transmitter coupled to the controller to transmit the at least one occurrence of the at least one type of arrhythmia. The system further comprises a programmer. The programmer includes a processor to control the programmer, a programmer receiver coupled to the processor to receive the at least one occurrence of the at least one type of arrhythmia, and a display that includes at least one graph showing the frequency of the at least one occurrence of the at least one type of arrhythmia over the predetermined period of time.

A further illustrative embodiment includes an exemplary data structure. The data structure comprises at least one count variable to contain a count of a frequency of the at least one type of arrhythmia. The data structure further comprises a recorded episode data structure to ascertain that at least one type of arrhythmia is present, wherein once the recorded episode data structure ascertains that at least one type of arrhythmia is present, the one count variable for the type of arrhythmia is incremented.

A further illustrative embodiment includes a programmer. The programmer comprises a processor to control the programmer, a programmer receiver coupled to the processor to receive at least one occurrence of at least one type of arrhythmia, and a display that includes at least one graph showing the frequency of at least one occurrence of at least one type of arrhythmia over the predetermined period of time.

A further illustrative embodiment includes a method of presenting at least one type of arrhythmia. The method comprises monitoring a heart rate over a first predetermined duration, triggering when the heart rate reaches a predetermined threshold over the first predetermined duration to define a detected arrhythmia episode, recording when the detected arrhythmia episode is sustained over a second predetermined duration and a therapy is applied, and displaying at least one graph to show the frequency of the detected arrhythmia episode over a predetermined period of time.

These and other embodiments, aspects, advantages, and features of the present invention will be set forth in part in the description which follows, and in part will become apparent to those skilled in the art by reference to the following description of the invention and drawings or by practice of the invention. The aspects, advantages, and features of the invention are realized and attained by means of the instrumentalities, procedures, and combinations particularly pointed out in the appended claims.

DETAILED DESCRIPTION

Figure 1A:
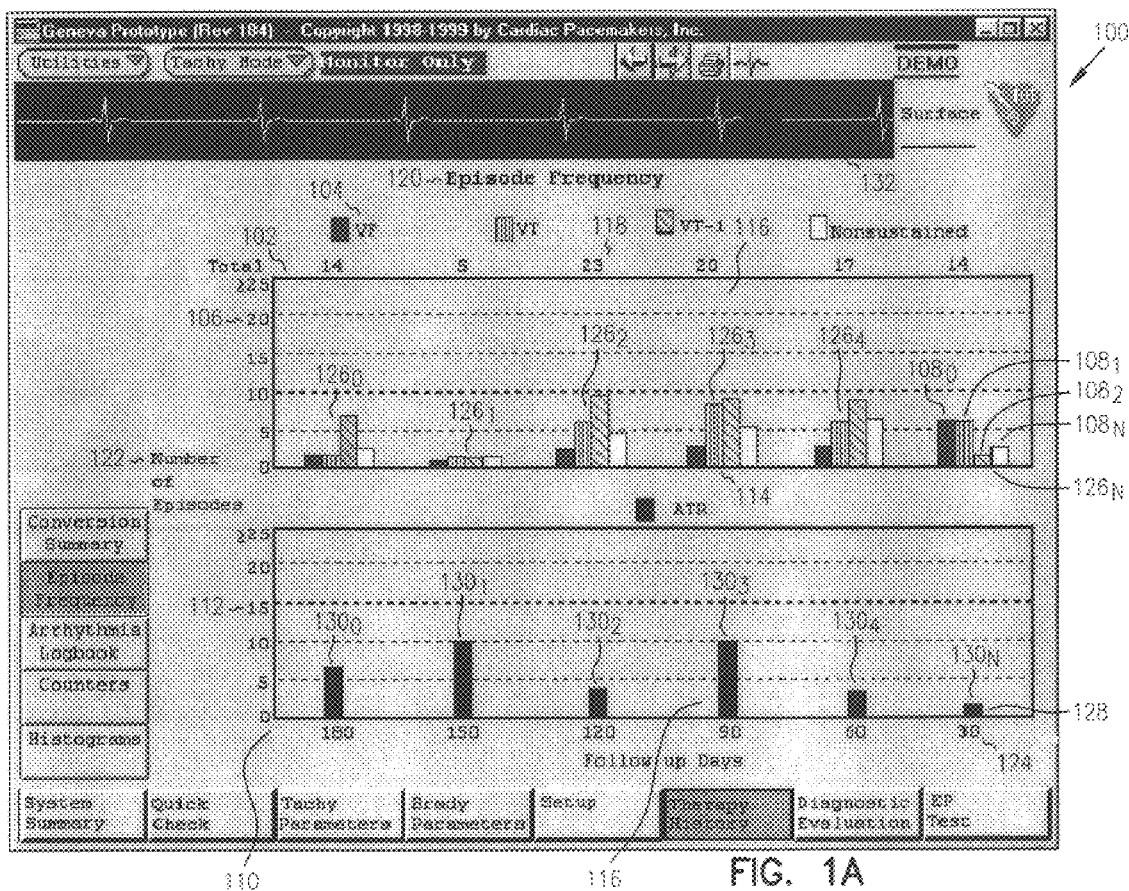
FIG. 1A is a pictorial diagram illustrating a display in accordance with one embodiment.

In the following detailed description of the invention, reference is made to the accompanying drawings that form a part hereof, and in which are shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, logical, and electrical changes may be made without departing from the scope of the present invention.

The embodiments described herein focus on visual communication of data to a professional, such as a physician, who is making a diagnostic or changing a therapy for a patient having an implantable medical device, such as a pacemaker, implantable cardioverter defibrillator, or defibrillator.

Implantable cardioverter defibrillators are designed to detect and provide therapy for various types of arrhythmia that include ventricular tachycardia and ventricular fibrillation. Each device may include a pulse generator to generate pulses that may be used in a therapy session. An external component, such as a programmer, allows interrogation and programming of the pulse generator, as well as access to the device's diagnostic features. Each device can be programmed to provide a variety of detection options. Each can also provide noninvasive diagnostic testing and therapy history data. In one embodiment, an implantable cardioverter defibrillator may also act as a pacer.

In the case of an implantable cardioverter defibrillator, the embodiments provide for a presentation that enables a physician to quickly analyze the history of shock therapy that has been applied to the patient by the implantable cardioverter defibrillator over a period of time. Certain conclusions that can be drawn from looking at the visual history provided by the embodiments include whether the patient is experiencing a lot of shock therapy, whether the shock therapy is applied infrequently, or whether the therapy is applied regularly. Based on conclusions drawn from the presentation of the embodiments, the physician may decide to adjust the therapy delivered by the implantable cardioverter defibrillator, or to medicate the patient with antiarrhythmic medications, or both.

FIG. 1A is a pictorial diagram illustrating a display in accordance with one embodiment. In this embodiment, the display 100 includes chart 102. In one embodiment, the display 100 is a real-time display. In one embodiment, chart 102 is a graph. In another embodiment, chart 102 is a column graph as shown in FIG. 1A. In another embodiment, the chart 102 is a bar graph. In another embodiment, the chart 102 is a line graph. In another embodiment, the chart 102 is a pie graph. In another embodiment, the chart 102 is an XY graph. In another embodiment, the chart 102 is an area graph. Other charts and graphs may be used without departing from the present invention. In all embodiments, the chart 102 visually presents the variation of a variable with respect to one or more other variables.

The graph 102 includes symbols $108_0$, $108_1$, $108_2$, . . . , and $108_N$. Each symbol is indicative of the type of arrhythmia that was detected by an implantable cardioverter defibrillator implanted in a patient. In one embodiment, the type of arrhythmia includes ventricular arrhythmia. In another embodiment, ventricular arrhythmia includes ventricular fibrillation, sustained ventricular tachycardia, or non-sustained ventricular tachycardia. In one embodiment, sustained ventricular tachycardia is understood to mean the inclusion of a detected ventricular tachycardia for a predetermined period of time for which an appropriate shock therapy was delivered. In another embodiment, non-sustained ventricular tachycardia is understood to mean the inclusion of a detected ventricular tachycardia for which shock therapy was not delivered because such detection did not meet additional criteria, such as the duration of the occurrence of the detected ventricular tachycardia.

In the chart 102, the symbol $108_0$ is indicative of detected episodes of ventricular fibrillation. The symbol $108_1$, is indicative of detected episodes of ventricular tachycardia. The symbol $108_2$ is indicative of detected episodes of user-defined ventricular tachycardia. The symbol $108_N$ is indicative of detected episodes of non-sustained ventricular tachycardia. In one embodiment, a user can define a zone of interest within a detection of ventricular tachycardia. When a ventricular tachycardia occurs within this zone of interest, its frequency may be recorded and displayed by the symbol $108_2$. The zone of interest includes a dependency on a user-programmed range of heart rates. In another embodiment, the user can define three zones of interest. In another embodiment, a zone is a range of heart rates that is programmed for each type of tachyarrhythmia that can be treated by a separate therapy prescription.

Symbols $108_0$, $108_1$, $108_2$, . . . , $108_N$ may be composed of diverse symbol types, colors, patterns, fills, and linewidths. In chart 102, these symbols are columns with distinguishing patterns and fills. The term symbol types is not limited to the column symbol as shown in FIG. 1A, but is inclusive of any symbols that can serve to visually communicate the frequency of detected episodes of a particular arrhythmia. The term colors is understood to mean the inclusion of gray scale.

Symbols $108_0$, $108_1$, $108_2$, . . . , $108_N$ may be grouped together in a cluster. In chart 102, clusters $126_0$, $126_1$, $126_2$, $126_3$, $126_4$, . . . , $126_N$ represent a time period when the episodes of various types of arrhythmia were detected. In one embodiment, the time period is about five months. In another embodiment, the time period is greater than about five months. In another embodiment, the time period is less than about five months.

The chart 102 includes a legend 104. The legend 104 explains the symbols on the chart 102. In one embodiment, the legend 104 explains the symbols on the chart 102 by associating a text label with a sample of the specific symbol.

The chart 102 includes numerical data label 106 on the ordinate of the chart 102. The data label 106 is indicative of the number of episodes of detected arrhythmia. In one embodiment, the numerical data in label 106 are selectively scaled based on the range of frequency of the detected episodes of various typies of arrhythmia.

The chart 102 includes gridlines 116. The gridlines 116 are placed at predetermined intervals to visually conmmunicate the level of frequency with respect to the symbols $108_0$., $108_1$, $108_2$, ..., $108_N$.

Figure 1B:
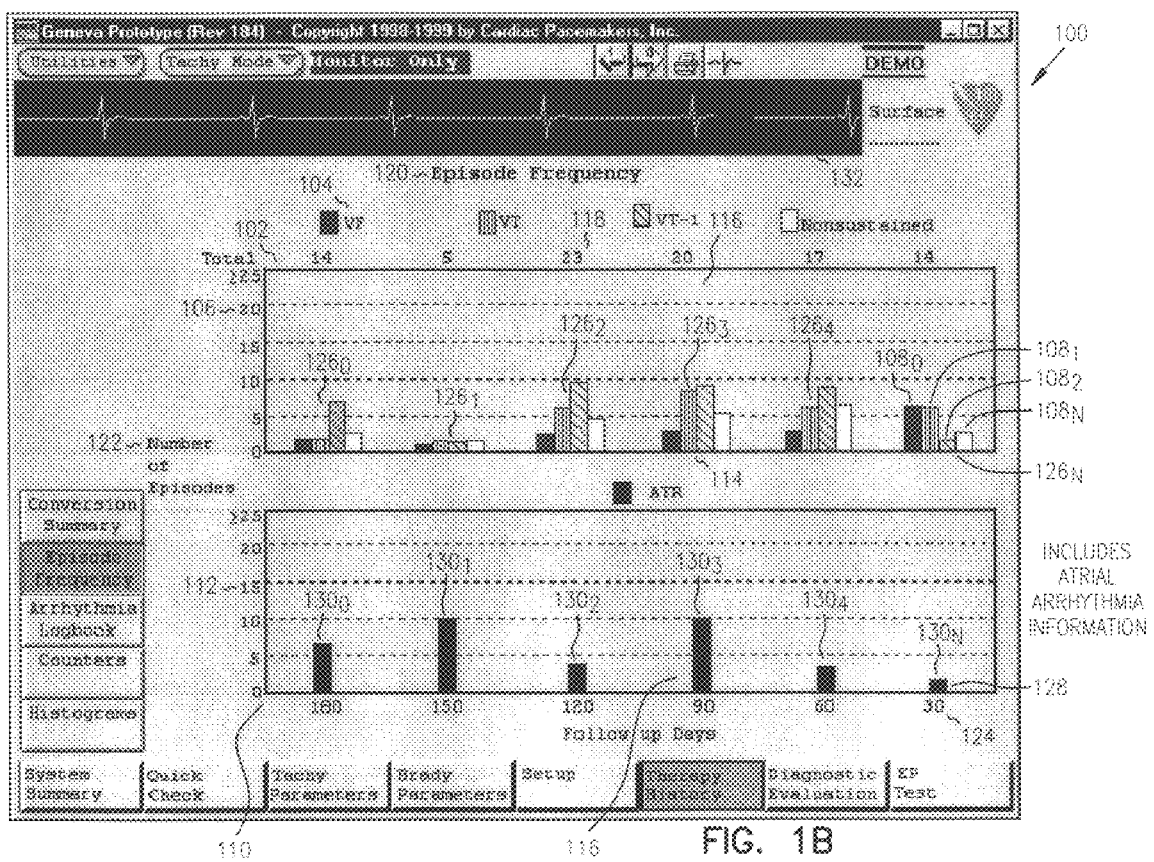
FIG. 1B is a pictorial diagram illustrating a display in accordance with one emobidment.

The display 100 also includes a chart 110. In one embodiment, the chart 110 contains graphical elements as described above and so the above description is incorporated here. In one embodiment, the chart 110 contains symbol 128. This symbol is indicative of the type of arrhythmia that was detected by an implantable cardiverter defibrillator implanted in a patient. In one embodiment, as demonstrated by FIG. 1B, the type of arrhythmia includes atrial arrhythmia. The chart 110 includes a legend 114, gridlines 116, numerical data label 112, and clusters $130_0$, $130_1$, $130_2$, $130_3$, $130_4$, ... $130_N$.

The display 100 includes a title 120. In one embodiment, this title is user-definable and may be placed at the top to be conspicuous. In another embodiment, the display 100 automatically displays a pre-set title 120. The title 120 serves to communicate the purpose of the display 100. The display 100 also includes a data title 122. This data title 122 serves to communicate the purpose of the numerical data labels 106 and 112.

The display 100 also includes an electrogram display 132. The electrogram display 132 shows intervals that are the time difference from beat to beat. The electrogram display 132 also shows markers. Markers are labels of the type of arrhythmia on the electrogram. For example, if ventricular tachycardia is on the electrogram, the region of the electrogram associated with this arrhythmia would be labeled VT. The electrogram display 132 may automatically provide electrogram channel display appropriate for the arrhythmia activities shown or other cardiac activities.

Figure 2:
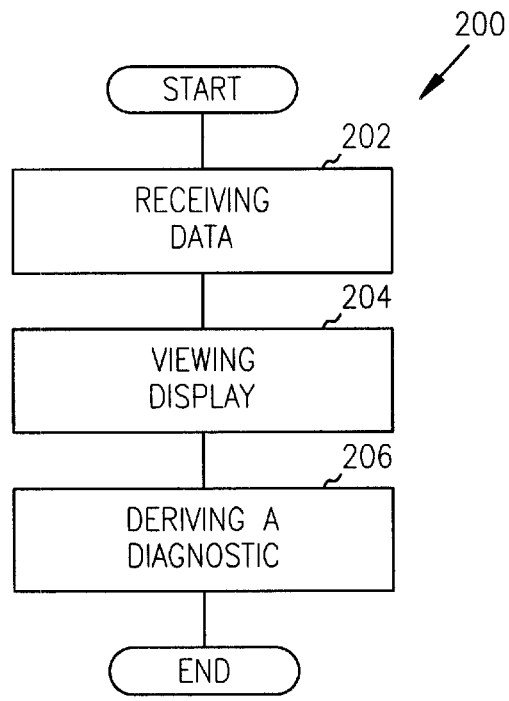
FIG. 2 is a flow diagram illustrating a method in accordance with one embodiment.

FIG. 2 is a flow diagram illustrating a method in accordance with one embodiment. The method 200 is usable by a professional, such as a physician, to diagnose a medical condition based on the data received from an implantable medical device. The method 200 begins at block 202 for receiving episode data that is stored in an implantable medical device, such as an implantable cardioverter defibrillator. Next, at block 204, such data is processed and correlated into a presentation that is viewable on a display. The display shows at least one graph showing the frequency of each detected type of arrhythmia that a patient has experienced over a predetermined period of time, such as five months. Next, at block 206, a physician makes a diagnostic based on such presentation and adjusts the implantable cardioverter defibrillator, or prescribes medicine, or both.

Figure 3:
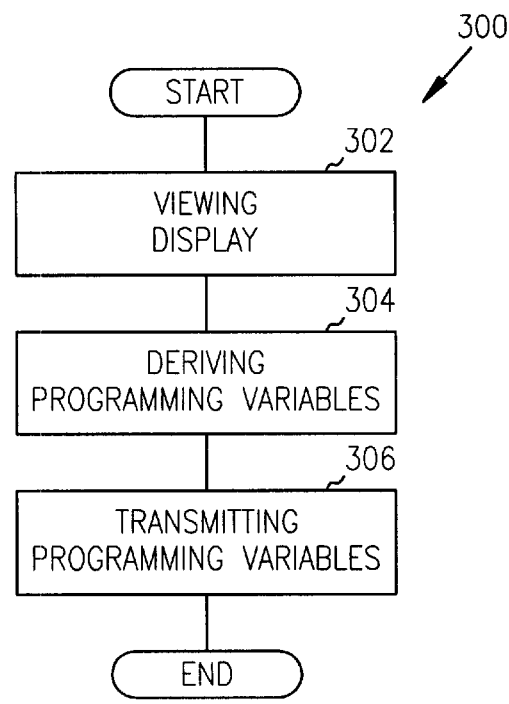
FIG. 3 is a flow diagram illustrating a method in accordance with one embodiment.

FIG. 3 is a flow diagram illustrating a method in accordance with one embodiment. Method 300 is usable by a professional, such as a physician, to diagnose a medical condition based on the data received from an implantable medical device to change the therapy that a patient has been receiving. The method 300 begins at block 302 where a physician can view a display that has at least one graph showing the frequency of each type of arrhythmia that the patient has experienced over a predetermined period of time, such as five months or greater. At block 304, the physician can derive a set of programming variable values based on his observation of the display. These programming variable values are used to reprogram the implantable medical device, such as an implantable cardioverter defibrillator. The reprogrammed implantable medical device would deliver a different therapy when a patient experiences a predetermined type of arrhythmia, such as ventricular fibrillation. At block 306, the set of programming variable values are transmitted to the implantable medical device so as to reprogram it. In one embodiment, such transmission is made through wireless telemetry techniques. In another embodiment, such transmission is made through wired telemetry techniques.

Figure 4:
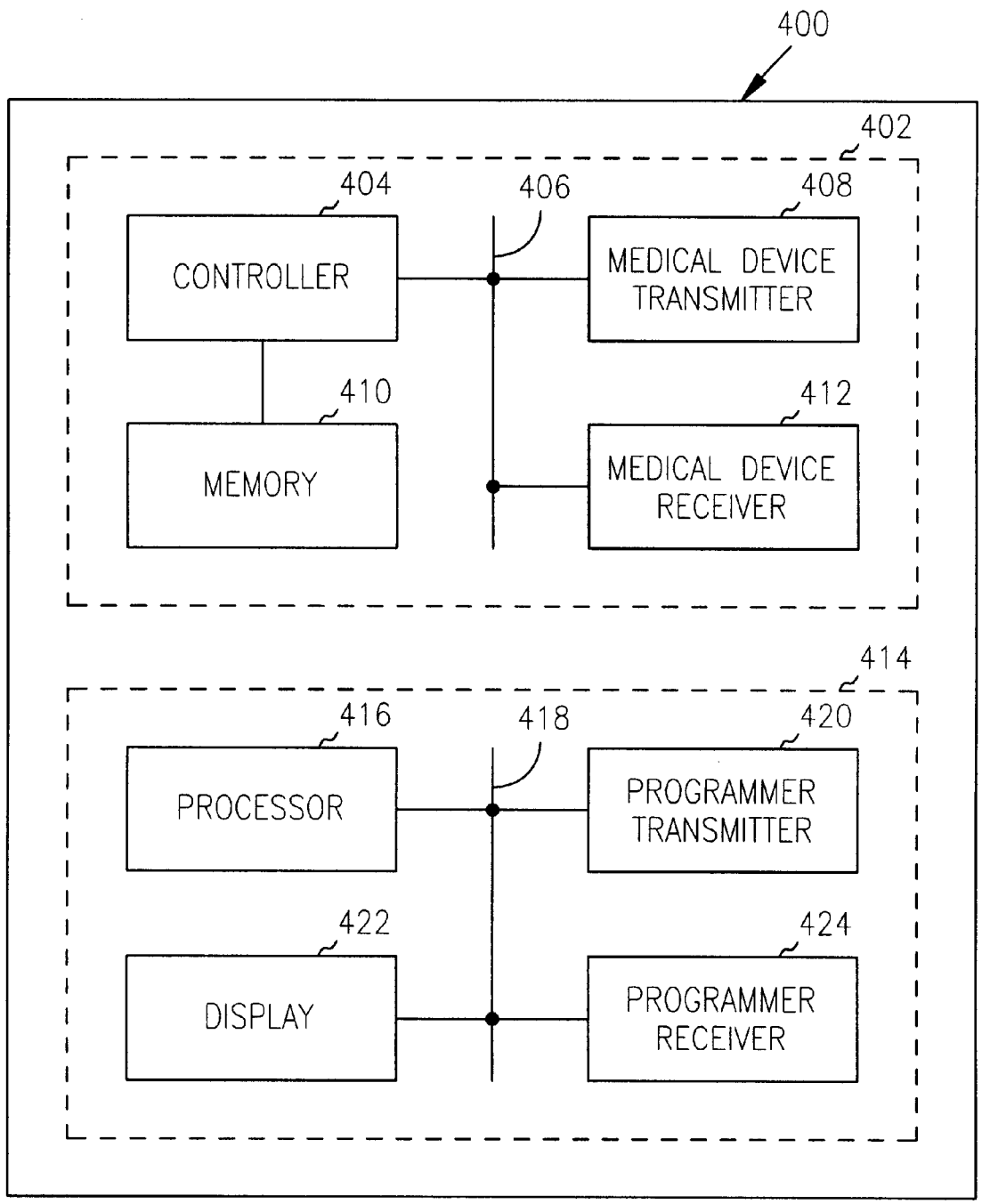
FIG. 4 is a block diagram illustrating a system in accordance with one embodiment.

FIG. 4 is a block diagram illustrating a system in accordance with one embodiment. The system 400 includes an implantable medical device 402. In one embodiment, implantable medical device 402 includes an implantable cardioverter defibrillator. The device 402 includes a controller 404 to control the device 402. The device 402 includes memory 410 that is coupled to the controller 404. In one embodiment, the memory 410 stores a count for each occurrence of each detected type of arrhythmia that the patient experiences, and perhaps, sensed details of each arrhythmia event. The device 402 includes a transmitter 408 that is coupled to the controller 404. In one embodiment, the transmitter 408 transmits each count upon a request by a user, such as a physician. The device 402 includes a receiver 408 that is coupled to the controller 404. In one embodiment, the receiver 408 is receptive to reprogramming instructions from a user, such as a physician.

The system 400 includes a programmer 414. The programmer 414 includes a processor 416 to control the programmer 414. The programmer 414 includes a coupling network 418, such as a bus. The programmer 414 includes a programmer receiver 424. In one embodiment, the programmer receiver 424 is receptive to a transmission from the transmitter 408 to receive each count for each occurrence of each detected type of arrhythmia that the patient experiences. The programmer 414 includes a programmer transmitter 420. In one embodiment, the programmer transmitter 420 is used to reprogram the implantable medical device 402 to apply a different therapy when a type of arrhythmia is detected. The programmer transmitter 420 can also be used to transmit a detection zone of interest which the device 402 classifies after detecting a type of arrhythmia. The programmer 414 includes a display 422. The display 422 is capable of displaying at least one graph showing the frequency of each detected type of arrhythmia that the patient has experienced over a predetermined period of time, such as five months or greater. The display 422 is capable of displaying the frequency associated with the types of arrhythmia specified within the zone of interest. In one embodiment, the zone of interest is specifiable by a user, and is can be transmitted by the programmer transmitter 420 to the device 402.

Figure 5A:
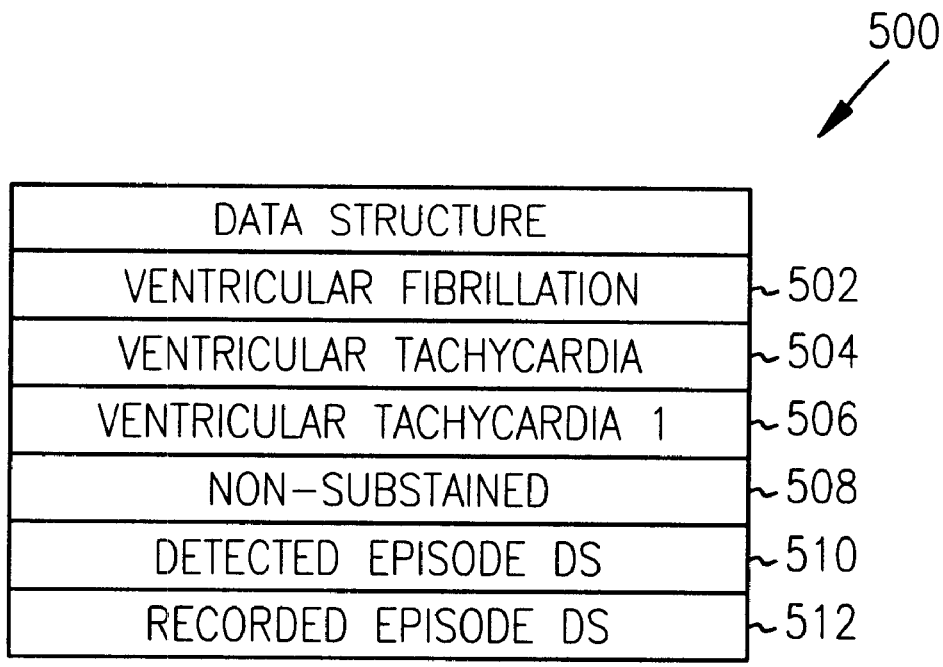
FIGS. 5A–B are block diagrams illustrating data structures in accordance with one embodiment.
Figure 5B:
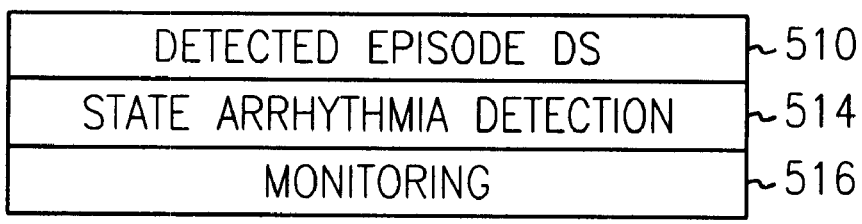

FIGS. 5A–B are block diagrams illustrating data structures in accordance with one embodiment. FIG. 5A shows a data structure 500 to record at least one frequency of at least one detected type of arrhythmia. In one embodiment, the data structure can be transmitted from an implantable medical device back to a programmer so that each frequency of each detected type of arrhythmia can be displayed. In another embodiment, only a part of the data structure is transmitted back to the programmer. In one embodiment, the data structure 500 is objectoriented, such as a class.

The data structure 500 includes a variable "ventricular fibrillation" 502 to store a count of each occurrence of detected ventricular fibrillation that a patient experiences over a predetermined period of time, such as five months. The data structure 500 includes a variable "ventricular tachycardia" 504 to store a count of each occurrence of detected ventricular tachycardia that a patient experiences over the same predetermined period of time as used in variable 502. The data structure 500 includes a variable "ventricular tachycardia 1" 506 to store a count of each occurrence of a detected user-defined zone of interest for ventricular tachycardia that a patient experiences over the same predetermined period of time as used in variable 502. The data structure 500 includes a variable "non-sustained ventricular tachycardia" 508 to store a count of each occurrence of detected arrhythmia that did not meet other criteria for a therapy to be delivered to the patient. In another embodiment, variables 502, 504, and 506 store a count of each occurrence of a different detected user-defined zone of interest.

In one embodiment, the data structure 500 includes a data structure entitled detected episode 510. In another embodiment, the data structure 500 contains a pointer to the detected episode data structure 510. In one embodiment, the detected episode data structure 510 contains information that at least one type of arrhythmia has been detected based on a number of criteria, such as heart rate. The data structure 500 also includes a data structure entitled recorded episode 512. In another embodiment, the data structure 500 contains a pointer to the recorded episode data structure 512. In one embodiment, the recorded episode data structure 512 contains information to confirm that the detected arrhythmia is present according to additional criteria, such as the duration of the detected arrhythmia. If the recorded episode data structure 512 confirms that a detected arrhythmia is present in the patient, one of the appropriate variables 502, 504, 506, or 508 will be incremented to reflect the occurrence of the detected arrhythmia.

FIG. 5B shows the data structure 510 in greater detail. The data structure 510 includes a state 514 to determine that at least one type of arrhythmia has been detected. In one embodiment, the data structure 510 is object-oriented. In this embodiment, the data structure 510 is a class and further includes a method of monitoring the heart rate to determine if it has reached a certain predetermined threshold, such as above 160 beats per minute. When the heart rate has reached the predetermined threshold, the state 514 is updated to indicate that the particular type of arrhythmia has been detected.

Figure 6:
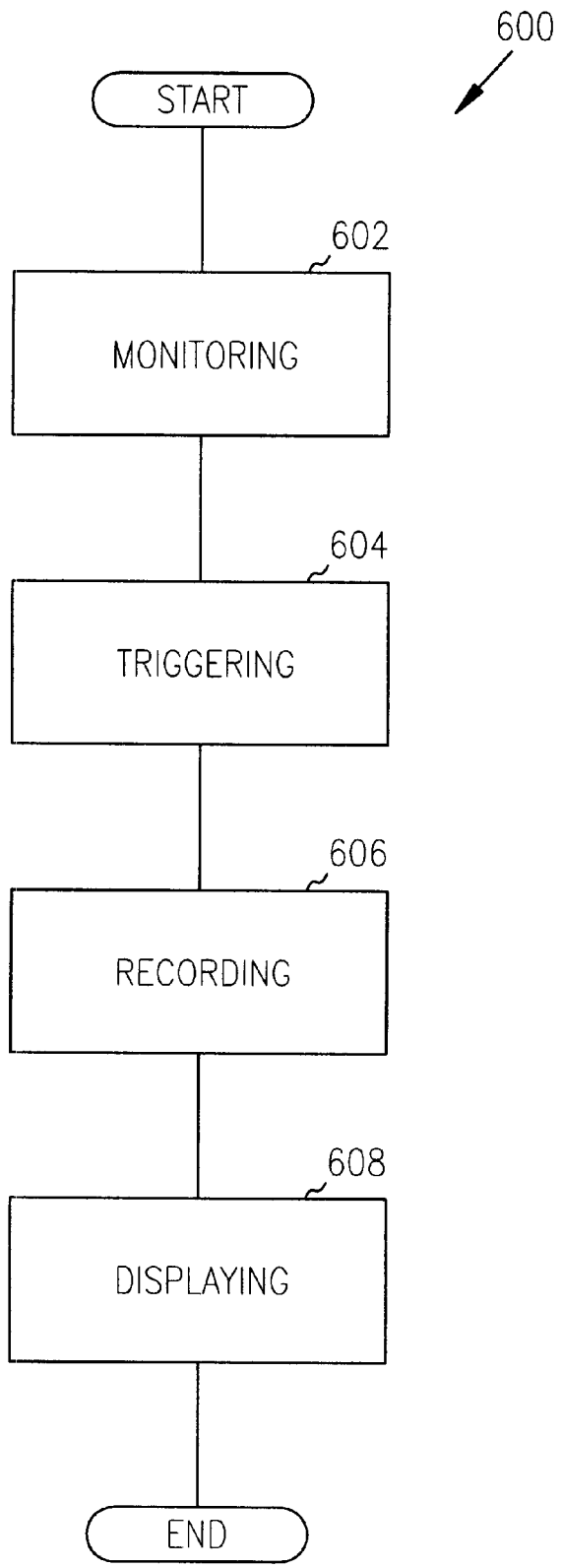
FIG. 6 is a flow diagram illustrating a method in accordance with one embodiment.

FIG. 6 is a flow diagram illustrating a method in accordance with one embodiment. The method 600 begins at block 602. Block 602 monitors a heart rate over a duration that is predetermined. If the heart rate reaches at least one certain threshold, such as over 160 beats per minute, block 604 triggers and depending on the heart rate and other factors, the type of arrhythmia is classified as being detected.

Next, the method 600 continues to monitor the detected arrhythmia and apply additional criteria at block 606. For example, if the detected arrhythmia episode is sustained over another predetermined duration of time, a therapy may be applied. Depending on the outcome of the therapy, the block 606 records and classifies the occurrence of the particular type of arrhythmia. In one embodiment, the block 606 simply records the occurrence of the detected type of arrhythmia as detected in block 604.

In one embodiment, the above flow may be iterated for a predetermined period of time, such as five months. In another embodiment, only individual blocks, such as block 602 or block 604, or both are iterated. At the end of this period, the recorded data is transmitted to a display. At block 608, the display reformats the data to present a visual presentation that is easy to understand to a professional, such as a physician.

CONCLUSION

Thus, systems, devices, structures, and methods have been described to visually present data from an implantable medical device to a professional, such as a physician.

Although the specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. It is to be understood that the above description is intended to be illustrative and not restrictive. Combinations of the above embodiments and other embodiments will be apparent to those of skill in the art upon reviewing the above description. The scope of the invention includes any other applications in which the above structures and fabrication methods are used. Accordingly, the scope of the invention should only be determined with reference to the appended claims, along with the full scope of equivalents to which such claims are entitled.

What is claimed is:

1. A display comprising:
   a first graph to show a frequency of at least one type of ventricular arrhythmia over a predetermined amount of time; and
   a second graph to show a frequency of at least one type of atrial arrhythmia over the predetermined amount of time.

2. The display of claim 1, wherein the at least one type of ventricular arrhythmias includes ventricular fibrillation, sustained ventricular tachycardia, and non-sustained ventricular tachycardia.

3. The display of claim 2, wherein the first graph is capable of showing a sustained ventricular tachycardia based upon a detection zone programmatically determined by a user.

4. The display of claim 1, wherein the predetermined amount of time is about five months or greater.

5. The display of claim 1, wherein the display selectively scales the first graph based on the frequency of the at least one type of ventricular arrhythmia over the predetermined amount of time.

6. The display of claim 1, wherein the display selectively scales the second graph based on the frequency of the at least one type of atrial arrhythmia over the predetermined amount of time.

7. The display of claim 1, wherein the first graph is a column graph, wherein the ordinate of the column graph is scaled to the frequency of the at least one type of ventricular arrhythmia over the predetermined amount of time, and wherein the abscissa of the column graph shows a column for each type of ventricular arrhythmia.

8. The display of claim 7, wherein each column showing each type of ventricular arrhythmia is diverse is color.

9. The display of claim 8, wherein color includes gray scale.

10. The display of claim 7, wherein each column showing each type of ventricular arrhythmia is diverse in pattern.

11. The display of claim 7, wherein each column showing each type of ventricular arrhythmia is diverse in pattern and color.

12. The display of claim 11, wherein the color includes gray scale.

13. The display of claim 1, wherein the second graph is a column graph, wherein the ordinate of the column graph is scaled to the frequency of the at least one type of atrial arrhythmia over the predetermined amount of time, and wherein the abscissa of the column graph shows a column for each type of atrial arrhythmia.

14. The display of claim 13, wherein each column showing each type of atrial arrhythmia is diverse is color.

15. The display of claim 14, wherein color includes gray scale.

16. The display of claim 13, wherein each column showing each type of atrial arrhythmia is diverse in pattern.

17. The display of claim 13, wherein each column showing each type of atrial arrhythmia is diverse in pattern and color.

18. The display of claim 17, wherein the color includes gray scale.

19. The display of claim 1, wherein the first graph includes a legend to show the at least one type of ventricular arrhythmia.

20. The display of claim 1, wherein the second graph includes a legend to show the at least one type of ventricular arrhythmia.

21. The display of claim 1, wherein the display is a real-time display.

22. The display of claim 1, wherein at least one graph among the first graph and the second graph is formed from data from an implantable medical device.

23. A method of performing a medical diagnostic, the method comprising:
    receiving data stored in an implantable medical device;
    viewing a display that includes at least one graph showing the frequency of at least one type of arrhythmia over a predetermined period of time, wherein the at least one graph is formed from the data received from the implantable medical device; and
    deriving a diagnostic based at least on the at least one graph.

24. The method of claim 23, wherein viewing the display includes viewing the at least one graph showing the frequency of ventricular arrhythmia, wherein ventricular arrhythmia includes ventricular fibrillation, sustained ventricular tachycardia, and non-sustained ventricular tachycardia.

25. The method of claim 24, wherein viewing the display includes viewing another graph showing the frequency of atrial arrhythmia, wherein atrial arrhythmia includes atria tachycardia.

26. The method of claim 24, wherein viewing the display includes viewing the at least one graph that is capable of showing a sustained ventricular tachycardia based on a detection zone programmatically determined by a user.

27. The method of claim 23, wherein viewing the display includes viewing the at least one graph showing the frequency of the at least one type of arrhythmia over a period of about five months or greater.

28. A method of therapy, the method comprising:
    viewing a display that includes at least one graph showing the frequency of at least one type of arrhythmia over a predetermined period of time;
    deriving a set of programming variable values based at least on the at least one graph to program an implantable medical device; and
    transmitting the set of programming variable values to the implantable medical device so as to apply a therapy when a patient experiences a predetermined type of arrhythmia.

29. The method of claim 28, wherein viewing the display includes viewing the at least one graph showing the frequency of ventricular arrhythmia, wherein ventricular arrhythmia includes ventricular fibrillation, sustained ventricular tachycardia, and non-sustained ventricular tachycardia.

30. The method of claim 29, wherein viewing the display includes viewing another graph showing the frequency of atrial arrhythmia, wherein atrial arrhythmia includes atria tachycardia.

31. The method of claim 29, wherein viewing the display includes viewing the at least one graph that is capable of showing a sustained ventricular tachycardia based on a detection zone programmatically determined by a user.

32. The method of claim 28, wherein viewing the display includes viewing the at least one graph showing the frequency of the at least one type of arrhythmia over a period of about five months or greater.

33. A system comprising:
    an implantable medical device that includes:
        a controller to control the implantable medical device;
        memory coupled to the controller to store at least one occurrence of at least one type of arrhythmia over a predetermined period of time; and
        a medical device transmitter coupled to the controller to transmit the at least one occurrence of the at least one type of arrhythmia; and
    a programmer that includes:
    a processor to control the programmer;
    a programmer receiver coupled to the processor to receive the at least one occurrence of the at least one type of arrhythmia; and
    a display that includes at least one graph showing the frequency of the at least one occurrence of the at least one type of arrhythmia over the predetermined period of time.

34. The system of claim 33, wherein the at least one graph shows the frequency of ventricular arrhythmia, wherein ventricular arrhythmia includes ventricular fibrillation, sustained ventricular tachycardia, and non-sustained ventricular tachycardia.

35. The system of claim 34, wherein the display includes another graph showing the frequency of atrial arrhythmia, wherein atrial arrhythmia includes atria tachycardia.

36. The system of claim 33, wherein the implantable medical device further comprises a medical device receiver, wherein the programmer further comprises a programmer transmitter, and wherein the programmer is capable of defining at least one detection zone for sustained ventricular tachycardia.

37. The system of claim 36, wherein the programmer transmitter transmits the at least one detection zone to the medical device receiver.

38. The system of claim 34, wherein the at least one graph is capable of showing the sustained ventricular tachycardia based on the at least one detection zone.

39. A data structure to record a frequency of at least one type of arrhythmia so as to allow a presentation of the frequency of the at least one type of arrhythmia, the data structure comprising:

at least one count variable to contain a count of a frequency of the at least one type of arrhythmia; and a recorded episode data structure to ascertain that the at least one type of arrhythmia is present, wherein once the recorded episode data structure ascertains that the at least one type of arrhythmia is present, the at least one count variable for the at least one type of arrhythmia is incremented.

40. The data structure of claim 39, wherein the data structure further comprises a detected episode data structure to determine that the at least one type of arrhythmia has been detected.

41. The data structure of claim 40, wherein the detected episode data structure further comprises a state to indicate whether the at least one type of arrhythmia has been detected.

42. The data structure of claim 41, wherein the detected episode data structure is object-oriented, wherein the detected episode data structure further comprises an act of monitoring a heart rate to determine if the heart rate reached a predetermined threshold, wherein when the heart rate has reached a predetermined threshold, the state of the detected episode data structure indicates that the at least one type of arrhythmia has been detected.

43. A programmer to program an implantable medical device, the programmer comprising:

a processor to control the programmer;

a programmer receiver coupled to the processor to receive at least one occurrence of at least one type of arrhythmia; and a display that includes at least one graph showing the frequency of the at least one occurrence of the at least one type of arrhythmia over the predetermined period of time.

44. A method of presenting at least one type of arrhythmia, the method comprising:

monitoring a heart rate over a first predetermined duration;

triggering when the heart rate reaches a predetermined threshold over the first predetermined duration to define a detected arrhythmia episode;

recording when the detected arrhythmia episode is sustained over a second predetermined duration and a therapy is applied; and displaying at least one graph to show the frequency of the detected arrhythmia episode over a predetermined period of time.

45. The method of claim 43, wherein the acts of monitoring, triggering, or recording are iterated over the predetermined period of time before displaying the at least one graph.

* * * * *

UNITED STATES PATENT AND TRADEMARK OFFICE
CERTIFICATE OF CORRECTION

PATENT NO. : 6,449,504 B1
DATED : September 10, 2002
INVENTOR(S) : Conley et al.

Page 1 of 4

It is certified that error appears in the above-identified patent and that said Letters Patent is hereby corrected as shown below:

<u>Title page,</u>
Item [56], under U.S. PATENT DOCUMENTS, insert

| | | | |
|---|---|---|---|
| -- 4,529,401 | 7/1985 | Leslie et al. ………… … | 604/131 |
| 5,578,063 | 11/1996 | Bocek et al. ……… …. | 607/5 |
| 5,603,331 | 2/1997 | Heemels et al. …… …. | 128/696 |
| 5,674,249 | 10/1997 | de Coriolis et al. …… | 607/5 |
| 5,792,203 | 8/1998 | Schroeppel…………. | 607/30 |
| 6,091,990 | 7/2000 | Hsu et al. …………… | 607/5 |
| 6,253,102 | 6/2001 | Hsu et al. ……..……. | 600/515 |
| 6,289,244 | 9/2001 | Conley et al. …….….. | 607/27 |
| 6,289,248 | 9/2001 | Conley et al. ……….. | 607/59 |
| 6,301,503 | 10/2001 | Hsu et al. …………... | 607/30 --. |

<u>Column 8,</u>
Line 60, delete "diverse is" and insert -- diverse in --, therefor.

<u>Column 9,</u>
Line 10, delete "diverse is" and insert -- diverse in --, therefor.

<u>Columns 9-12</u>
Delete claims 23-45:
"23. A method of performing a medical diagnostic, the method comprising:
    receiving data stored in an implantable medical device;
    viewing a display that includes at least one graph showing the frequency of at least one type of arrhythmia over a predetermined period of time, wherein the at least one graph is formed from the data received from the implantable medical device; and
    deriving a diagnostic based at least on the at least one graph.

24. The method of claim 23, wherein viewing the display includes viewing the at least one graph showing the frequency of ventricular arrhythmia, wherein ventricular arrhythmia includes ventricular fibrillation, sustained ventricular tachycardia, and non-sustained ventricular tachycardia.

25. The method of claim 24, wherein viewing the display includes viewing another graph showing the frequency of atrial arrhythmia, wherein atrial arrhythmia includes atria tachycardia.

26. The method of claim 24, wherein viewing the display includes viewing the at least one graph that is capable of showing a sustained ventricular tachycardia based on a detection zone programmatically determined by a user.

27. The method of claim 23, wherein viewing the display includes viewing the at least one graph showing the frequency of the at least one type of arrhythmia over a period of about five months or greater.

UNITED STATES PATENT AND TRADEMARK OFFICE
CERTIFICATE OF CORRECTION

PATENT NO. : 6,449,504 B1
DATED : September 10, 2002
INVENTOR(S) : Conley et al.

It is certified that error appears in the above-identified patent and that said Letters Patent is hereby corrected as shown below:

28. A method of therapy, the method comprising:
    viewing a display that includes at least one graph showing the frequency of at least one type of arrhythmia over a predetermined period of time;
    deriving a set of programming variable values based at least on the at least one graph to program an implantable medical device; and
    transmitting the set of programming variable values to the implantable medical device so as to apply a therapy when a patient experiences a predetermined type of arrhythmia.

29. The method of claim 28, wherein viewing the display includes viewing the at least one graph showing the frequency of ventricular arrhythmia, wherein ventricular arrhythmia includes ventricular fibrillation, sustained ventricular tachycardia, and non-sustained ventricular tachycardia.

30. The method of claim 29, wherein viewing the display includes viewing another graph showing the frequency of atrial arrhythmia, wherein atrial arrhythmia includes atria tachycardia.

31. The method of claim 29, wherein viewing the display includes viewing the at least one graph that is capable of showing a sustained ventricular tachycardia based on a detection zone programmatically determined by a user.

32. The method of claim 28, wherein viewing the display includes viewing the at least one graph showing the frequency of the at least one type of arrhythmia over a period of about five months or greater.

33. A system comprising:
    an implantable medical device that includes:
    a controller to control the implantable medical device;
    memory coupled to the controller to store at least one occurrence of at least one type of arrhythmia over a predetermined period of time; and
    a medical device transmitter coupled to the controller to transmit the at least one occurrence of the at least one type of arrhythmia; and
        a programmer that includes:
            a processor to control the programmer;
            a programmer receiver coupled to the processor to receive the at least one occurrence of the at least one type of arrhythmia; and
            a display that includes at least one graph showing the frequency of the at least one occurrence of the at least one type of arrhythmia over the predetermined period of time.

34. The system of claim 33, wherein the at least one graph shows the frequency of ventricular arrhythmia, wherein ventricular arrhythmia includes ventricular fibrillation, sustained ventricular tachycardia, and non-sustained ventricular tachycardia.

35. The system of claim 34, wherein the display includes another graph showing the frequency of atrial arrhythmia, wherein atrial arrhythmia includes atria tachycardia.

36. The system of claim 33, wherein the implantable medical device further comprises a medical device receiver, wherein the programmer further comprises a programmer transmitter, and wherein the programmer is capable of defining at least one detection zone for sustained ventricular tachycardia.

37. The system of claim 36, wherein the programmer transmitter transmits the at least one detection zone to the medical device receiver.

UNITED STATES PATENT AND TRADEMARK OFFICE
CERTIFICATE OF CORRECTION

PATENT NO. : 6,449,504 B1
DATED : September 10, 2002
INVENTOR(S) : Conley et al.

It is certified that error appears in the above-identified patent and that said Letters Patent is hereby corrected as shown below:

38. The system of claim 34, wherein the at least one graph is capable of showing the sustained ventricular tachycardia based on the at least one detection zone.

39. A data structure to record a frequency of at least one type of arrhythmia so as to allow a presentation of the frequency of the at least one type of arrhythmia, the data structure comprising:
    at least one count variable to contain a count of a frequency of the at least one type of arrhythmia; and
    a recorded episode data structure to ascertain that the at least one type of arrhythmia is present, wherein once the recorded episode data structure ascertains that the at least one type of arrhythmia is present, the at least one count variable for the at least one type of arrhythmia is incremented.

40. The data structure of claim 39, wherein the data structure further comprises a detected episode data structure to determine that the at least one type of arrhythmia has been detected.

41. The data structure of claim 40, wherein the detected episode data structure further comprises a state to indicate whether the at least one type of arrhythmia has been detected.

42. The data structure of claim 41, wherein the detected episode data structure is object-oriented, wherein the detected episode data structure further comprises an act of monitoring a heart rate to determine if the heart rate reached a predetermined threshold, wherein when the heart rate has reached a predetermined threshold, the state of the detected episode data structure indicates that the at least one type of arrhythmia has been detected.

43. A programmer to program an implantable medical device, the programmer comprising:
    a processor to control the programmer;
    a programmer receiver coupled to the processor to receive at least one occurrence of at least one type of arrhythmia; and
    a display that includes at least one graph showing the frequency of the at least one occurrence of the at least one type of arrhythmia over the predetermined period of time.

UNITED STATES PATENT AND TRADEMARK OFFICE
CERTIFICATE OF CORRECTION

PATENT NO.    : 6,449,504 B1
DATED         : September 10, 2002
INVENTOR(S)   : Conley et al.

It is certified that error appears in the above-identified patent and that said Letters Patent is hereby corrected as shown below:

44. A method of presenting at least one type of arrhythmia, the method comprising:
    monitoring a heart rate over a first predetermined duration;
    triggering when the heart rate reaches a predetermined threshold over the first predetermined duration to define a detected arrhythmia episode;
    recording when the detected arrhythmia episode is sustained over a second predetermined duration and a therapy is applied; and
    displaying at least one graph to show the frequency of the detected arrhythmia episode over a predetermined period of time.

45. The method of claim 43, wherein the acts of monitoring, triggering, or recording are iterated over the predetermined period of time before displaying the at least one graph."

Signed and Sealed this

First Day of July, 2003

JAMES E. ROGAN
*Director of the United States Patent and Trademark Office*